(12) United States Patent
Chapin et al.

(10) Patent No.: US 7,970,476 B2
(45) Date of Patent: Jun. 28, 2011

(54) METHOD AND APPARATUS FOR GUIDING MOVEMENT OF A FREELY ROAMING ANIMAL THROUGH BRAIN STIMULATION

(75) Inventors: John K. Chapin, Atlantic Beach, NY (US); Sanjiv K. Talwar, Brooklyn, NY (US); Shaohua Xu, Brooklyn, NY (US); Emerson S. Hawley, Brooklyn, NY (US)

(73) Assignee: The Research Foundation of the State University of New York, Albany, NY (US)

( * ) Notice: Subject to any disclaimer, the term of this patent is extended or adjusted under 35 U.S.C. 154(b) by 630 days.

(21) Appl. No.: 10/361,441

(22) Filed: Feb. 10, 2003

(65) Prior Publication Data

US 2003/0199944 A1 Oct. 23, 2003

Related U.S. Application Data

(60) Provisional application No. 60/355,050, filed on Feb. 8, 2002.

(51) Int. Cl.
*A61N 1/08* (2006.01)
(52) U.S. Cl. .................................................. 607/48
(58) Field of Classification Search .................. 607/1, 2, 607/48, 49, 60, 115, 116; 600/544, 545; 340/573.3; 119/712, 720, 908
See application file for complete search history.

(56) References Cited

U.S. PATENT DOCUMENTS

| | | | | |
|---|---|---|---|---|
| 3,857,364 A | | 12/1974 | Miller, Jr. | |
| 4,802,482 A | | 2/1989 | Gonda et al. | |
| 4,852,573 A | * | 8/1989 | Kennedy | 600/377 |
| 5,002,053 A | * | 3/1991 | Garcia-Rill et al. | 607/49 |
| 5,411,965 A | * | 5/1995 | Reid et al. | 514/279 |
| 5,566,645 A | * | 10/1996 | Cole | 119/712 |
| 6,066,163 A | | 5/2000 | John | |
| 6,109,269 A | | 8/2000 | Rise et al. | |
| 6,463,328 B1 | * | 10/2002 | John | 607/45 |
| 6,529,774 B1 | * | 3/2003 | Greene | 600/545 |
| 2002/0046713 A1 | * | 4/2002 | Otto | 119/200 |

OTHER PUBLICATIONS

Mori, Shigemi. "Integration of Posture and Locomotion in Acute Decerebrate Cats and in Awake, Freely Moving Cats." Process in Neurobiology, vol. 28, pp. 161-195, 1987.*

Erzurumlu et al. "Whisker-related neural patterns develop normally despite severe whisker defects in Msx2 knockout mice," Developmental Brain Research 132 (2001) pp. 107-111.*

(Continued)

*Primary Examiner* — Eric D. Bertram
(74) *Attorney, Agent, or Firm* — Scully, Scott, Murphy & Presser, P.C.

(57) ABSTRACT

Movement of a freely roaming animal (190), such as a rat, is guided using electric stimulation of the animal's brain. Cues are provided to the animal to move forward by stimulating a reward center of the brain. Cues are provided to the animal to change its direction by stimulating portions of the animal's brain that control right and left movements, such as a cortical representation of whiskers of the animal. Multi-channel, remotely controlled equipment (140, 145, 150, 350) may be carried by the animal to enable independent energizing of electrodes attached to different regions of the animal's brain. A transmitter carried by the animal may report back data to allow monitoring. A component may be carried by the animal for carrying out a mission, such as for search and rescue or surveillance. Groups of animals may be controlled in real-time by coordinating their movements and tracking their locations.

8 Claims, 6 Drawing Sheets

OTHER PUBLICATIONS

Search Report for PCT/US03/03810, Sep. 29, 2003.
Wheeling H. S., et al., "Detection Thresholds for Electrical Stimulation of Forebrain and Midbrain Loci in the Rat", *Brain Research*, Vo. 272, No. 1, Aug. 1, 1983, pp. 13-19, XP007901372.
Talwar, et al., "A controlled navigation/locomotion animal model using a machine-brain interface", Program No. 63.13, 2001 Neuroscience Meeting Planner, San Diego, CA: Society for Neuroscience, 2001, Online.
European Official Action dated Oct. 16, 2009.

* cited by examiner

US 7,970,476 B2

METHOD AND APPARATUS FOR GUIDING MOVEMENT OF A FREELY ROAMING ANIMAL THROUGH BRAIN STIMULATION

CROSS-REFERENCE TO RELATED APPLICATIONS

This application claims the benefit of U.S. Provisional Patent Application Ser. No. 60/355,050, filed Feb. 8, 2002, and incorporated herein by reference.

STATEMENT REGARDING FEDERALLY SPONSORED RESEARCH OR DEVELOPMENT

The Government may have rights in the invention.

BACKGROUND OF THE INVENTION

1. Field of Invention

The invention relates generally to the field of guiding the movement of animals and, more specifically, to a method and apparatus for guiding the movement of a freely roaming animal using electric stimulation of the animal's brain.

2. Description of Related Art

Humans have long sought to understand how the brain functions. Examination and testing of laboratory animals has been undertaken in this regard. Procedures used to train laboratory animals often incorporate operant learning paradigms in which the animals are taught to make particular responses to external cues (e.g., tones) in order to obtain rewards (e.g., food). Moreover, electrical stimulation in the central nervous system has long been a tool in neurophysiology. However, previous approaches were constrained to using electric cables to connect brain-implanted electrodes to an external stimulator. While in anesthetized animals cable connections are generally adequate, in wakeful animals (such as monkeys) they not only limit the subject's freedom of movement, but also may distract its attention or produce emotional distress. Limitations in cable length also confine the animal's movement to small 2-D spaces.

Accordingly, there is a need for a method and apparatus that enriches the scope of investigable behavioral paradigms and enables brain stimulation experiments in animals moving freely in large and complex 3-dimensional (3D) environments. Moreover, it would be desirable to be able to use such remotely guided animals for search and rescue, law enforcement, military and other purposes. The present invention addresses the above and other issues.

BRIEF SUMMARY OF THE INVENTION

The present invention describes a system and method for controlling the movement of a freely roaming animal using electric stimulation of the animal's brain.

In one aspect, the invention provides a miniaturized multi-channel digital tele-stimulation system that allows remote delivery of stimulations to multiple brain sites of an animal. New behavioral models can be developed based solely on brain stimulation for studying the neural correlates of spatial learning. Moreover, brain stimulation can be used to generate cues and rewards, where the rewards can act as cues as well, and reinforcement contingencies can be arranged so that a human operator or computer can accurately guide the animal remotely, over arbitrarily defined routes and over varied 3-D terrains. The system may be built inexpensively using a commercially available radio modem and microprocessor components.

In a particular aspect of the invention, a method for guiding movement of a freely roaming animal includes providing cues to the animal to move forward by stimulating a reward center of the animal's brain, and providing cues to the animal to change its direction of movement by stimulating portions of the animal's brain which control left and right movements. A corresponding apparatus is also presented.

In another aspect, a method for guiding movement of a number of respective freely roaming animals includes providing cues to each animal to move forward by stimulating a reward center of the respective animal's brain, and providing cues to each animal to change its direction of movement by stimulating portions of the animal's brain which control left and right movements.

In another aspect, an apparatus for guiding movement of a freely roaming animal includes a remotely controlled receiver adapted to be carried by the animal, and energizing means responsive to the receiver for energizing electrodes implanted in different sites in the animal's brain to provide cues to the animal to move forward and to change its direction of movement. The receiver may be a multi-channel receiver that independently controls pairs of electrodes in response to user commands.

BRIEF DESCRIPTION OF THE DRAWINGS

These and other features, benefits and advantages of the present invention will become apparent by reference to the following text and figures, with like reference numbers referring to like structures across the views, wherein.

DETAILED DESCRIPTION OF THE INVENTION

By removing physical constraints associated with the delivery of cues and rewards, learning paradigms based on brain microstimulation can enable conditioning approaches that help transcend traditional boundaries in animal learning. Our experiments applied this paradigm to develop a behavioral model in which an experimenter is able to guide distant animals in the manner of intelligent robots.

Figure 1:
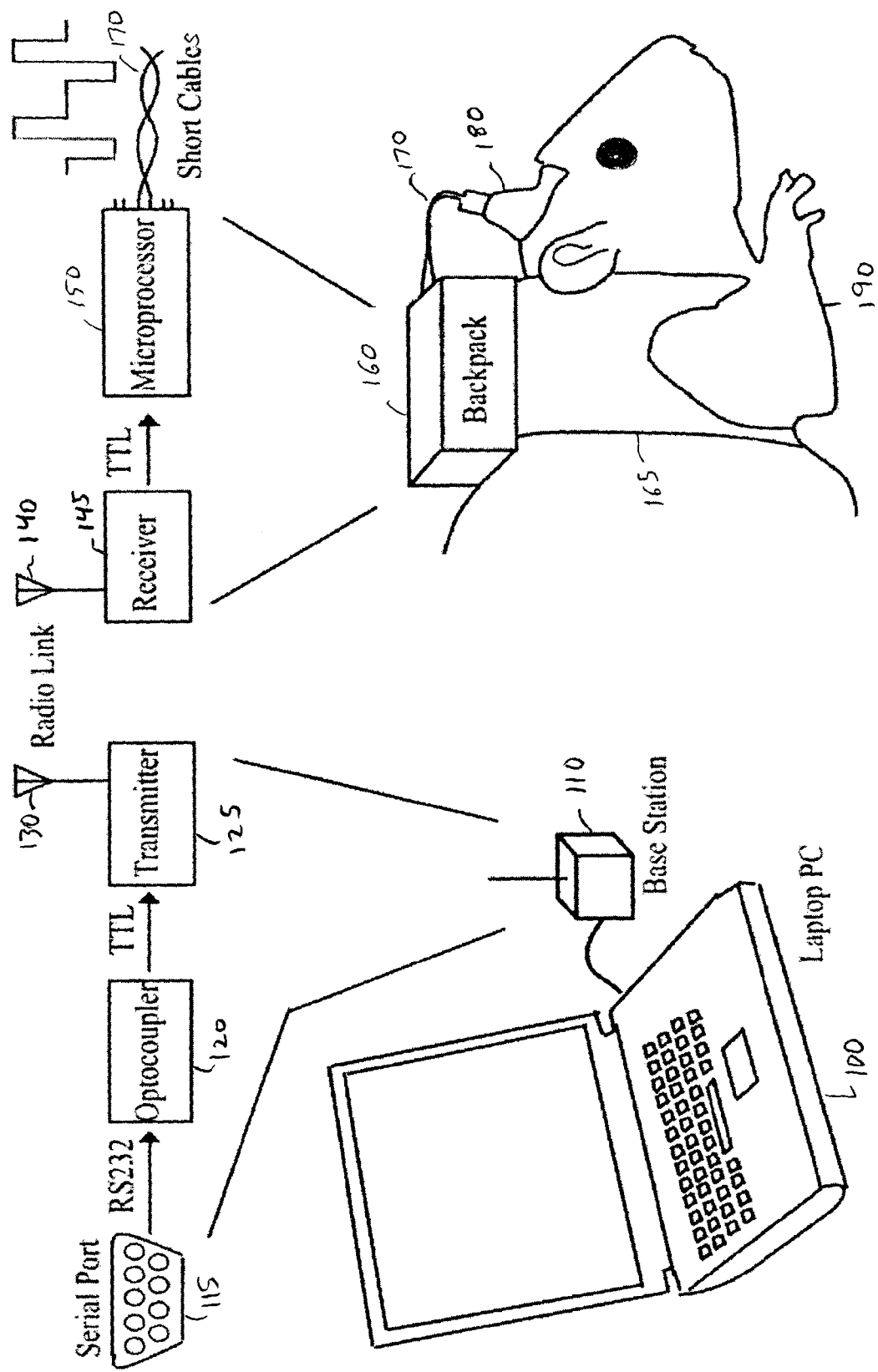
FIG. 1 illustrates a system for stimulating an animal's brain by remote control.

FIG. 1 illustrates an overview of a multichannnel tele-stimulation system showing the main components of the system and the signal flow. In one possible approach, a laptop personal computer 100 receives commands from an operator, e.g., via specific keystrokes, for guiding movement of a freely roaming animal 190, such as a rat. The laptop 100 sends a control signal to a base station 110 via a serial RS232 port 115. An optocoupler 120 processes the signal and provides it to a transmitter 125 as a transistor-transistor logic (TTL) signal. The transmitter 125 transmits the signal via antenna 130 and a radio link to an antenna 140 of a receiver 145, which is carried by the animal 190, such as in a backpack 160 which is secured to the animal using a harness 165 (available from Harvard Apparatus, Holliston, Mass.). The backpack 160 measured 48 mm×23 mm×19 mm and weighed 28 Gms, and is worn by the rat 190 by means of mating Velcro pieces.

The receiver 145 provides the received TTL signal to a microprocessor 150, which, in turn, controls electrodes that are implanted in the animal's brain. A skull-top adapter 180 on the animal houses the electrodes. A battery or other energizing means may be housed in the backpack 160, which send electrical current to the electrodes, e.g., energizes the electrodes, via short wires 170, to provide the desired stimulations to the brain sites to which the electrodes are attached. In practice, a pair of wires and electrodes is used for each brain site to be stimulated. Note that the configuration shown is merely one possible example, which has been found to be convenient for use by researchers. The particular remote control set-up can be adapted to particular applications. Moreover, additionally components may be carried by the backpack 160 or otherwise secured to the animal 190 including an upstream transmitter for communication video data back to the operator.

Depending on the site of brain stimulation, an electric stimulus can act as a cue or reward. Moreover, a reward stimulus can act as a cue as well. While studies investigating such phenomenon have generally been concerned with functional mechanisms of the nervous system, little thought has been given to the potential of behavioral paradigms constructed wholly around such focal brain stimulations. Our study used stimulation of a reward center of the brain to provide cues for moving forward, and stimulation of portions of the brain that control left and right movement as cues for moving left or right, respectively. For example, the reward center may include the medial forebrain bundle (MFB), ventral tegmental area, or other regions of the lateral hypothalamus. The portion of the brain for controlling left and right movement may include the somatosensory (SI) areas of the brain, such as cortical representations of left and right whiskers of the animal. In a particular experiment, SI and MFB stimulations, which act as virtual cues and rewards, respectively, were delivered to freely roaming rats. Behavioral contingencies were imposed so that an operator could accurately steer the animal, in real-time, over any arbitrarily specified 3-dimensional route and over any real-world terrain.

We implanted stimulating electrodes in the MFB, plus right and left SI whisker representations of a number of rats. The whisker representations mimic the rat's sensation of being lightly touched on the face. For example, if the rat has the sensation of being touched on the right side of the face, e.g., as if the rat was contacting a barrier on its right side, it will turn to the left to avoid the barrier. Similarly, a sensation on the left side of the face results in a right turn. The backpack 160, containing a microprocessor-based remote-controlled microstimulator, was then mounted on each animal. This allowed the operator using the laptop computer 100 to directly deliver brief trains of 80 µA stimulus pulses to any of the implanted brain-sites at distances up to 500 meters (typically ten, 0.5 msec, biphasic pulses at 100 Hz). Training the rats to navigate took ten sessions, during which the animals learned to interpret remotely received brain stimulation as instructions for directing their trajectory of locomotion. In a figure-8 maze, they first learned to obtain periodic MFB rewards (0.3-3 Hz) by running forward and turning correctly whenever left or right turning cues were issued; these cues were presented as "touch" stimulation of the left or right whiskers by stimulating their respective cortical representations. The animals were then placed in open environments that lacked the rectilinear structure and fixed choice points of the maze.

Figure 2:
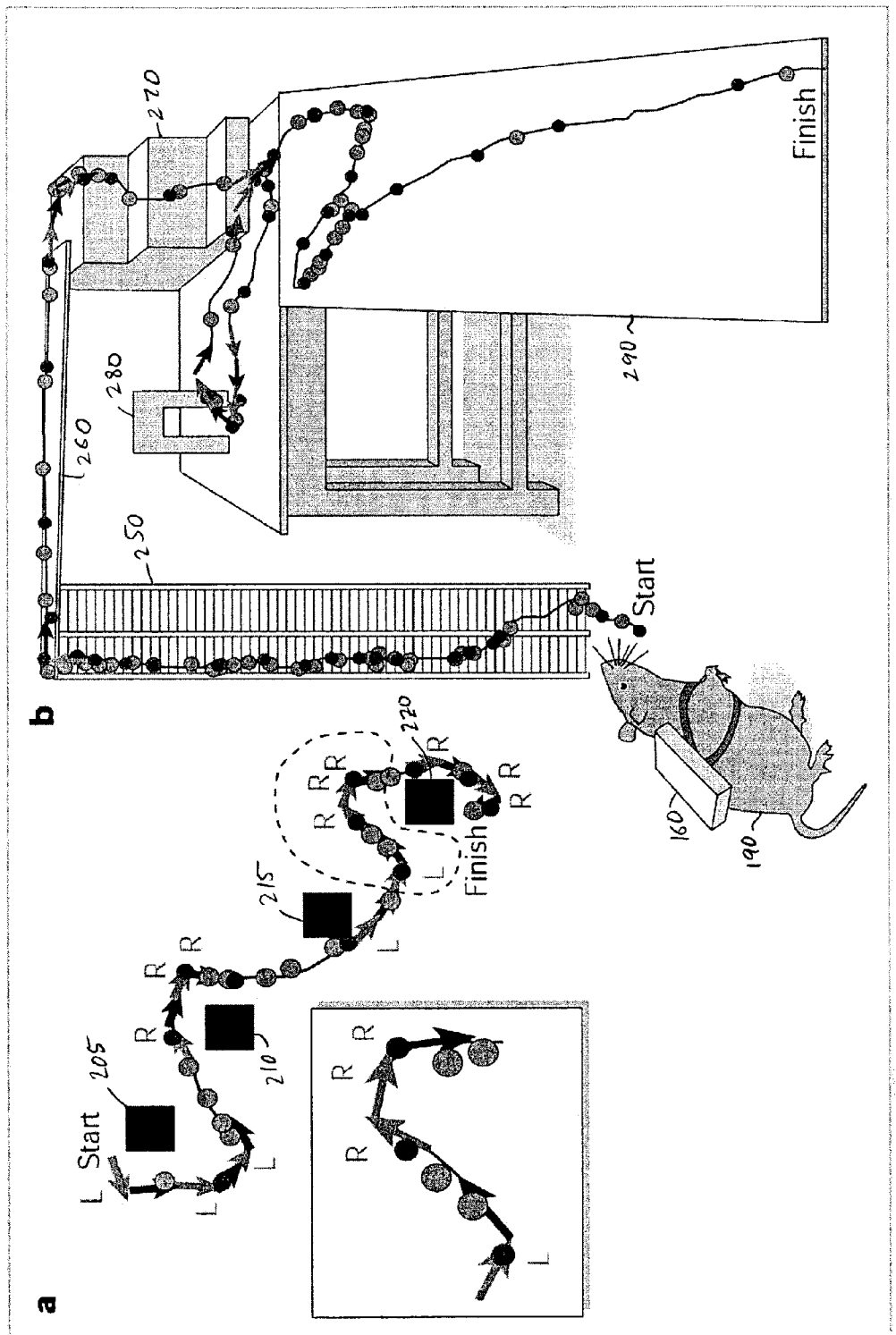
FIG. 2(a) illustrates movement of an animal over a two-dimensional course.
FIG. 2(b) illustrates movement of an animal over a three-dimensional course.

All rats generalized their responses to their new environments, running forward and turning instantaneously on cue (see FIG. 2(a)). They moved at speeds averaging 0.3 m/s and worked continuously for periods up to a 1-hour test limit. FIG. 2(a) illustrates movement of the animal from a start point to a finish point. The diagram was sketched from digitized video recordings. Dark shaded dots indicate the rat's head positions at one-second intervals. Light shaded dots indicate positions at which reward stimulations were administered to the MFB. Light colored arrows, labeled "R" or "L", indicate positions at which right or left directional cues, respectively, were issued. Black arrows indicate positions 0.5 sec after directional commands. Obstacles 205, 210, 215 and 220 created a slalom course. The inset indicates details of the events that took place inside the dashed-line region.

Navigation over 3-D structures was achieved by incorporating a unique behavioral attribute of MFB stimulation that reflected the known "priming" qualities of MFB stimulation. We observed that MFB stimulation not only reinforced forward locomotion but also initiated and motivated further locomotion. Thus an MFB reward, itself, served as an effective GO-forward cue. On approaching objects such as a high step, GO-forward MFB stimulation would induce the rats to climb or to descend from it. As a rule, the number of such stimulations required was proportional to the difficulty of the obstacle ahead (see FIG. 2(b)). The arrow and dot depictions in FIG. 2(b) were obtained using the key as discussed in connection with FIG. 2(a). Here, the rat 190 is guided over a 3-dimensional obstacle course. The animal was instructed to climb a vertical ladder 250, cross a narrow ledge 260, descend a flight of steps 270, pass through a hoop 280, and a descend a steep (70 degree) ramp 290. Two rounds of high-density MFB stimulation were required to guide the rat successfully down the ramp, demonstrating the motivational qualities of MFB-stimulation.

Superimposing GO-forward MFB stimulations onto the standard schedule was thus sufficient to steer the rats through a wide variety of complex, novel, and changing terrains. Our rats were easily guided through pipes, across elevated runways and ledges, and were induced to climb or jump from any surface that offered sufficient purchase (e.g., trees). The animals were also guided to systematically explore large collapsed concrete rubble piles and directed through environments that they would normally avoid, such as brightly lit wide-open outdoor arenas.

Our results show that "virtual" learning, by directly accessing the central substrates of cues and rewards, can effectively expand the scope of the operant method. It draws its chief benefit from its ability to dissociate explicit schedule variables such as cues and rewards from the physical variables normally associated with their delivery, lending a freedom from the mechanical and parametric constraints on learning imposed by particular physical settings. The rewarding efficacy of MFB stimulation is relatively non-satiating and animals need not initiate consummatory behaviors to obtain them. Since virtual cues and rewards are perceived within a body-centered frame of reference, they may facilitate the learning of behaviors independent of the external environment. It may also be possible to increase the "bandwidth" conditionable information by stimulating through a multiplicity of sites in the brain, thus increasing the richness of elicited animal behaviors.

The specific behavioral model presented here—a guided animal—has implications for new neurophysiological studies into directed animal navigation. The model also represents a new extension for operant conditioning into useful real-world applications. Combined with electronic sensor and navigation technology, the guided rat can be developed into an effective robot platform possessing several natural advantages over current mobile robots. Moreover, the added ability to remotely receive and interpret brain activity allows the guided rat to function both as mobile robot and biological sensor. This ability can be provided using appropriate sensors and data transmitting equipment carried by the rat.

Figure 3:
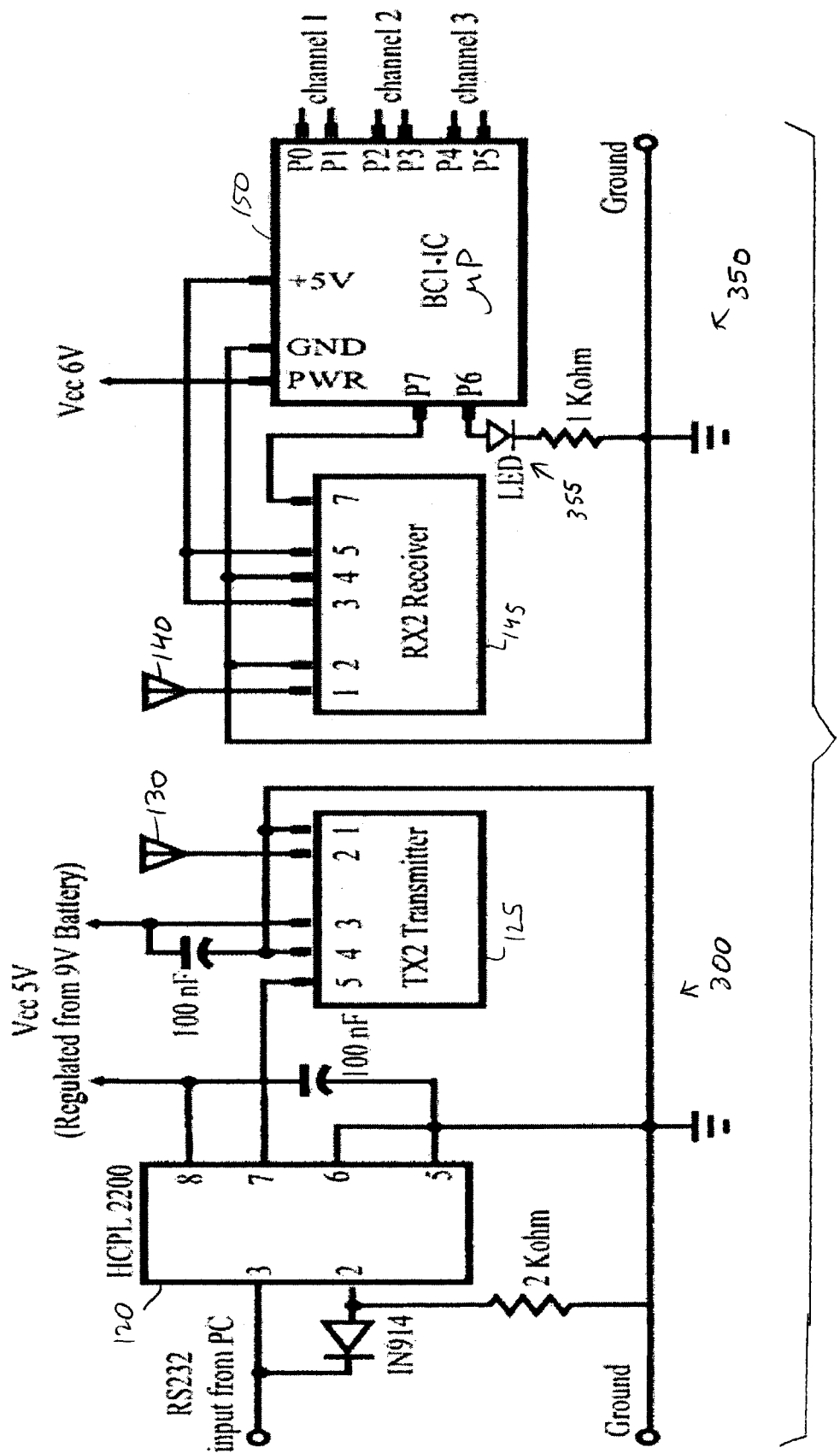
FIG. 3 illustrates a schematic diagram of circuits for a base station transmitter, and for a receiver carried by an animal.

FIG. 3 illustrates a schematic diagram of circuits for a base station transmitter and a receiver. In one possible approach, the animal's brain is stimulated using a multi-channel remote control system that allows independent stimulation of each electrode and therefore each associated brain region via each channel. Note that the channels may be provided in various ways, e.g., on separate carrier frequencies in a frequency division multiplex, and/or in separate time slices in a time division multiplex. Other various approaches for remotely controlling the electrodes will be apparent to those skilled in the art. Moreover, when multiple animals are controlled, appropriate techniques can be used to ensure that only the intended animal is controlled, e.g., such as assigning frequencies or time slices to specific animals. Spread spectrum communications may also be used, where spreading and despreading codes are assigned for communications to specific animals. The movements of the multiple animals may be coordinated to achieve a specific goal. For example, if the animals are used to provide surveillance of a building, each animal can be guided to a specific, different part of the building. The cues can thus be provided to the animals to coordinate their movements.

The invention provides a multi-channel telemetry brain microstimulation system that provides a small, light, efficient and reliable electrical stimulation platform, with flexibility for experimental designs. The system includes two major components: the base station transmitter 125 connecting through the serial port 115 to the PC 100, and a receiver-microprocessor 145, 150 integrated into a backpack 160 that is carried by the animal 190, or otherwise secured to the animal, e.g., using adhesive, or implanted in the animal, such as under the animals skin.

In one possibility, the PC 100 issues ASCII stimulation command strings, each containing an identifying header and desired parameters. The microprocessor 150 translates the command, which is relayed by the transmitter 125 and the receiver 145, into biphasic TTL pulses to the specified channel. Oscilloscope recordings shows that a stimulator associated with the receiver 145 executes the stimulation commands with high fidelity and performs reliably even in complex environments. A three-channel system was tested for controlling three pairs of electrodes, one for stimulating the MFB, and one each for the left and right side SI whisker stimulations. However, this system is upgradeable to sixteen or more channels by upgrading the microprocessor. The flexibility in programming enables the system to deliver stimulation trains with different parameters to different channels sequentially.

The use of multiple channels for controlling brain stimulation allows multiple brain sites to be excited concurrently. The present invention further provides high transmission fidelity, reduced size and weight of the receiver that is implanted or mounted on the animal, and reduced power requirements at the transmitter and receiver. Moreover, the charge-balanced biphasic pulses provided by the invention avoid electrolytic tissue injury and electrode damage that can occur with monophasic pulses.

The system delivers brief trains of electrical stimulation to three brain locations, each implanted with a pair of electrodes. A program running on the laptop PC 100 specifies stimulation parameters. The transmitter 125 sends out digital commands to the receiver 145 and microprocessor 150 on the rat's backpack 160. The microprocessor 150 executes the incoming command, resulting in an output of a train of biphasic TTL pulses to the specified brain location.

The PC program, written in BASIC, configures the serial port 115 to output stimulation-commands encoded by specific keystrokes (keystrokes "j", "k" and "l" specified which of the three implanted brain locations are stimulated). Instead of pressing keys on a laptop computer, a dedicated controller with press buttons, joystick or the like could be used. For each brain location, the parameters of stimulation—the number of biphasic pulses in a train, its frequency and the duration of each pulse—could be specified. The commands were sent as an ASCII string, at 2400 baud, from the PC to the transmitter 125 via the serial port 115. A short header (e.g. "U", "U") was included to quiet inter-transmission noise and to establish timing.

The transmitter circuit, shown generally at 300 in FIG. 3, was built around a UHF transmitter (TX2, Radiometrix, Watford, UK) powered by a 5V supply regulated from a 9-volt battery. First, the serial port's RS232 signals were converted to TTL level signals using an Agilent HCPL 2200 optocoupler and then sent to the TX2 transmitter 125. A quarter wavelength whip antenna 130 broadcast the RF signal. The circuit 300 was put into an aluminum enclosure, which served as circuit ground and RF ground plane. The TX2 module 125 is a two stage surface acoustic wave (SAW) controlled, FM modulated transmitter that transmits at up to 40 kbps. It is available in 433.93 MHz and 418 MHz versions, both of which we have employed at the same time, with no cross talk.

The backpack circuitry, shown generally at 350 in FIG. 3, was assembled on a printed circuit board. Its main components were a receiver 145 (RX2, 5V version, Radiometrix) and a microprocessor 150 (Basic Stamp BS1 IC, Parallax Inc.) powered by a 6V 160-mAH lithium battery (2CR-1/3N). The receiver used a helical antenna 140 (as described in the RX2 documentation). The backpack circuitry 350 included a light-emitting diode (LED) 355 that provided direct visual verification of pulse delivery when the animals were freely moving. The input/output (I/O) pins of the microprocessor were connected to the skull-top adapter 180 that housed the electrode ends by short flexible detachable cables. Under load (15 mA total), without regulation, the 2CR-1/3N battery put out 5.5V. The microprocessor ceased working when the battery voltage fell to about 4.5V.

The Basic Stamp microprocessor 150 has eight tri-state programmable digital I/O pins (P0-P7): one of these was set to input the remotely received stimulation-command string and another for output to the LED indicator. The remaining six were paired to actuate three stimulus channels with biphasic pulse trains (thus each channel used two I/O pins to stimulate its respective electrode pair). The microprocessor was loaded with a PBASIC program that controlled stimulation as follows: when not in use, all electrode I/O pins were left in input mode ($Z \cong 1$ M$\Omega$) to prevent cross talk between electrodes. For stimulation, a pair of pins were opened for output ($Z \cong 20\Omega$) alternatively −5V applied first to one and then the other. Since this system was floating, applying this voltage to the first pin and then to the other resulted in a biphasic pulse. After stimulation, the pins were reset to input mode.

Under anesthesia, two teflon-coated stainless steel microwire electrodes (100 μm diameter), 1 mm apart, were stereotaxically implanted in the MFB (left side) and the whisker barrel fields (SI) of the two somatosensory cortices of five female Long-Evans rats. Stimulation experiments commenced five days after implantation.

Figure 4:
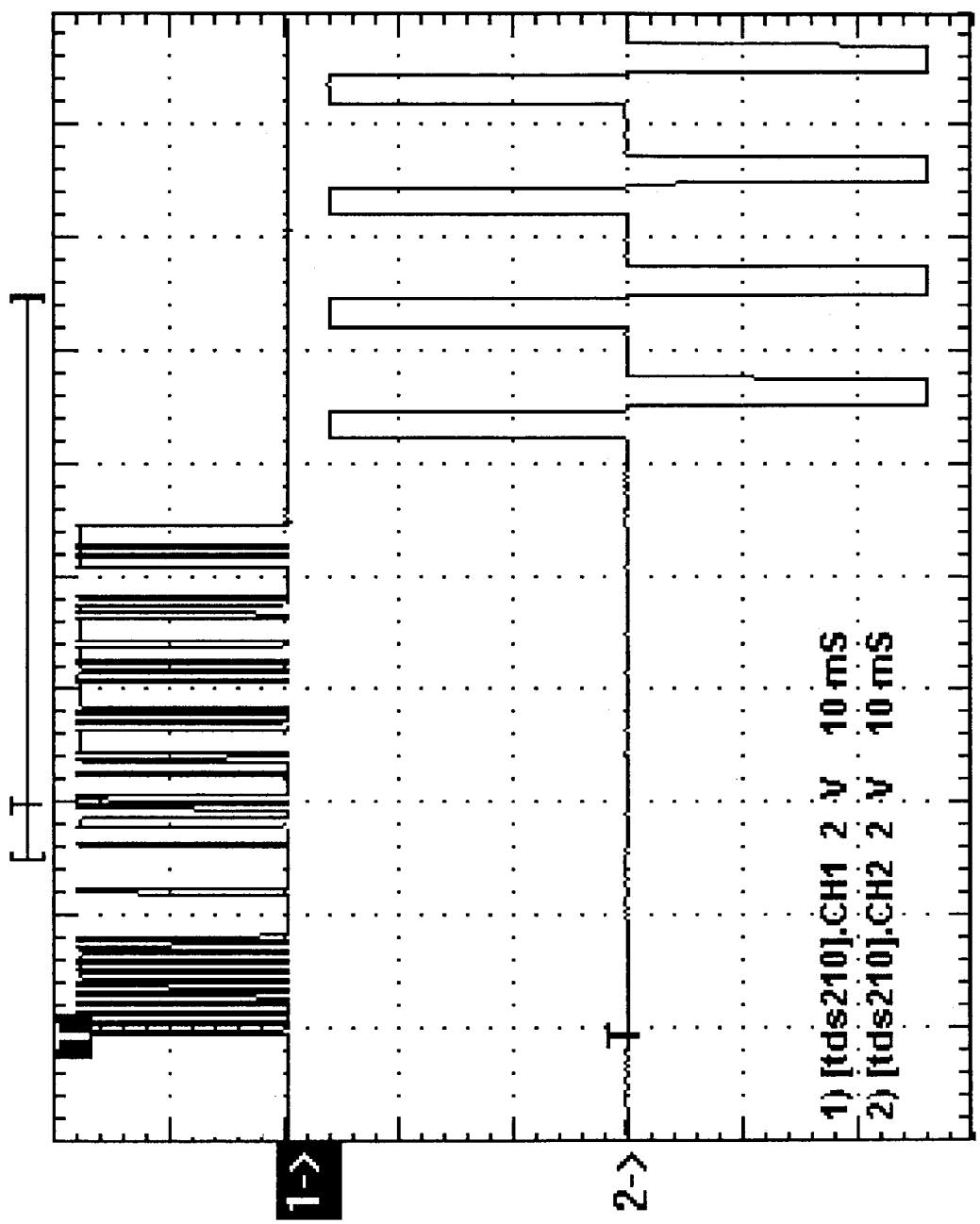
FIG. 4 illustrates a stimulation command string.

FIG. 4 illustrates an oscilloscope trace of an ASCII command string and the resulting train of biphasic pulses delivered to one stimulation channel. The telestimulator followed remotely received commands, which specified pulse frequency, pulse duration and the number of pulses within a train, with high fidelity. The microprocessor could deliver arbitrarily specified stimulus trains from distances as much as 300 meters, line of sight. The 6 V, 160-mAh lithium backpack battery system survived about seven hours of continuous stimulation (test stimulation consisted of stimulus trains delivered at 0.2 Hz; each train each had five biphasic pulses at 100 Hz with pulse duration 500 μseconds). The transmitter was able to work for several days (>7) using a 9 V lithium battery. It weighed 268 g and could easily be carried, along with the laptop, by the operator.

In particular, the ASCII stimulation command string (1) and output stimulation waveform (2) taken from the oscilloscope (TDS 210, Tektronix). Channel 1 shows the TTL command on transmitter input and channel 2 shows the biphasic stimulation waveform (biphasic stimulus pulses) on one of the three channels of the stimulator. It takes about 52 ms for the system to transmit and execute the command. The stimulation waveform follows the specified parameters: pulse number: 4, duration: 2.5 ms, and frequency: 100 Hz.

We next investigated the functional effectiveness of the system. Specifically, our goal was to evaluate the behavioral effectiveness of brain-stimulation delivered by direct 5V TTL output of the microprocessor. This was done by observing predictable behavioral responses consequent to stimulation of the MFB. MFB stimulation is rewarding and can be used to condition animal behaviors such as lever pressing. Connections were made between the microprocessor outputs and the implanted electrodes, and the rats were placed in a lever-equipped operant chamber in which a train of biphasic pulses to the MFB followed each lever press. Each train consisted of ten pulses delivered at 100 Hz with pulse duration 0.7 msec. Under this reinforcement schedule all subjects lever-pressed continuously, reaching pressing rates as high as 150/min over a 20 min period. Using an oscilloscope hooked across a resistor placed in series with the rat, we measured electrode impedance (at 100 Hz) to be around 50-100 KΩ. Thus, we estimated that the 5V TTL train delivered current amplitudes of around 50-100 μamps in the behaving animal.

Figure 5:
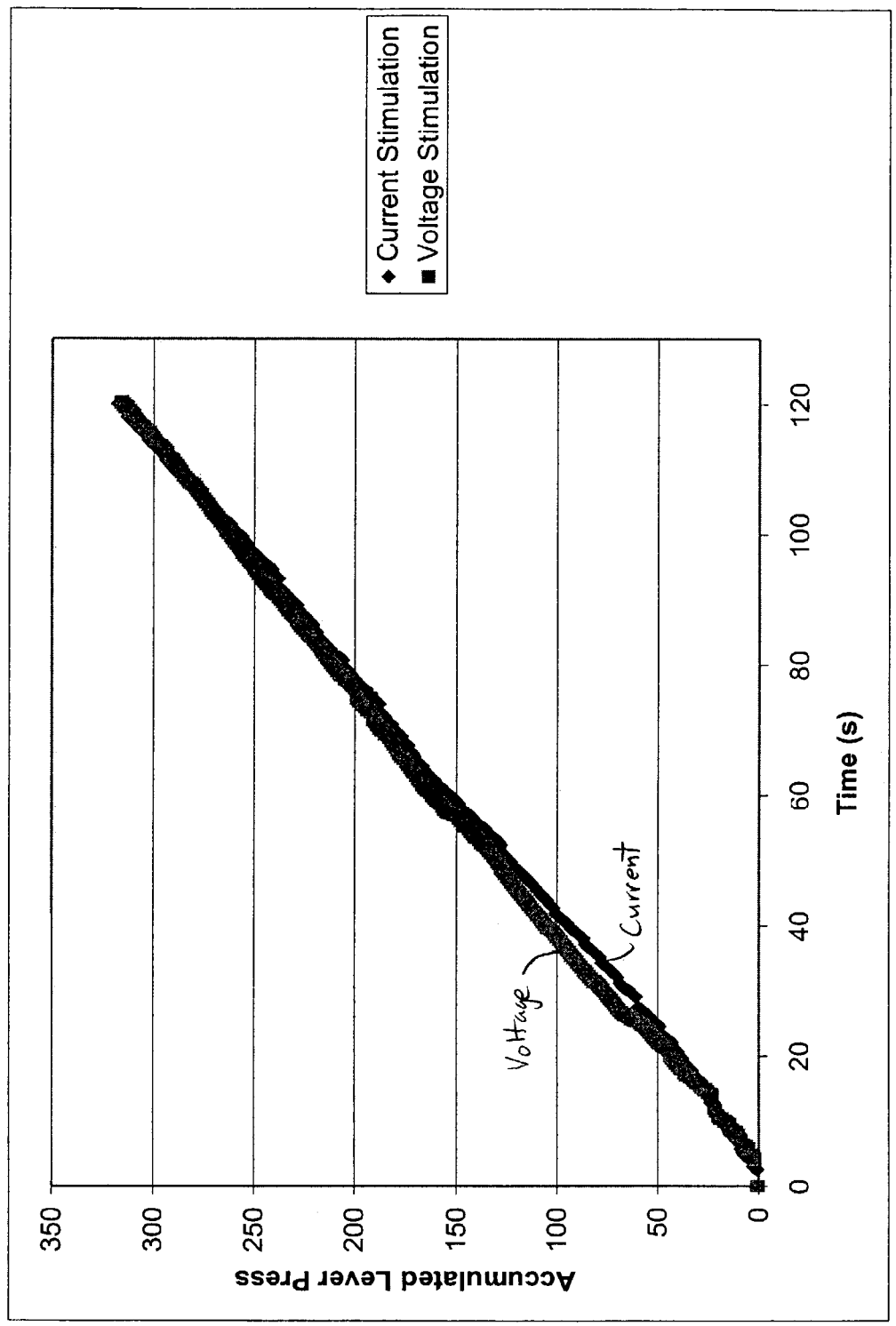
FIG. 5 illustrates a plot showing a number of lever presses by an animal when applying a constant voltage and a constant current source.

We compared the functional efficacy of the constant voltage 5V source in generating MFB stimulation rewards to that of a conventional constant current source which was set to deliver a comparable pulse train at 100 μamps (pulse duration 0.7 msec, frequency 100 Hz, 10 pulses). FIG. 5 shows two averaged cumulative frequency plots of the lever presses made by one rat over a two-minute period using both the constant voltage (light shaded line) and the constant current source (black line). The plots obtained using these two techniques are similar in that they almost overlap. We concluded that the telestimulator provided the reliability and stationarity of stimulation behavioral effect equal to that of a constant current stimulator set at 100 μamps.

For field-testing, the backpack was mounted on the rats. The animals were first trained to move forward continuously to obtain periodic MFB stimulation. Thereafter, stimulation of SI cortex (five pulses delivered at 100 Hz with pulse duration 0.5 msec) served as directional cues, in that the animals learned to turn left or right depending on which SI cortex was stimulated. Cortical representations of left or right whiskers of the animal were stimulated to effect a rightward or leftward change, respectively, in the direction of movement. Under this basic reinforcement contingency, we found that the rats could be accurately guided over arbitrarily specified 3-D routes at considerable distances away, showing that both cues and rewards were reliably delivered by the telestimulation system. The rats worked without tiring for periods up to a one-hour test limit.

The telestimulation system advantageously provides multiple output channels in a single package to allow simultaneous bipolar or monopolar stimulation of multiple brain sites, and it is both reliable and robust as a brain-stimulator. A special feature of the system is that it accomplished this task using conventional TTL pulses. The use of tri-state logic circuitry to generate biphasic stimulus pulses allows an experimenter to stimulate chronically over long time periods while avoiding the electrolytic injury caused by unidirectional currents. Another feature of the system is that the backpack containing the receiver, microprocessor and battery is small, light and power efficient, allowing it to be carried by small animals over relatively long time periods. These advantages are attributable to the relative simplicity of the device, which uses a commercially available microprocessor to provide well-controlled multichannel stimulus patterns. In our case, the backpack microprocessor was programmed to carry out specific stimulation patterns, but a simple reprogramming would allow almost any pattern to be specified.

Figure 6:
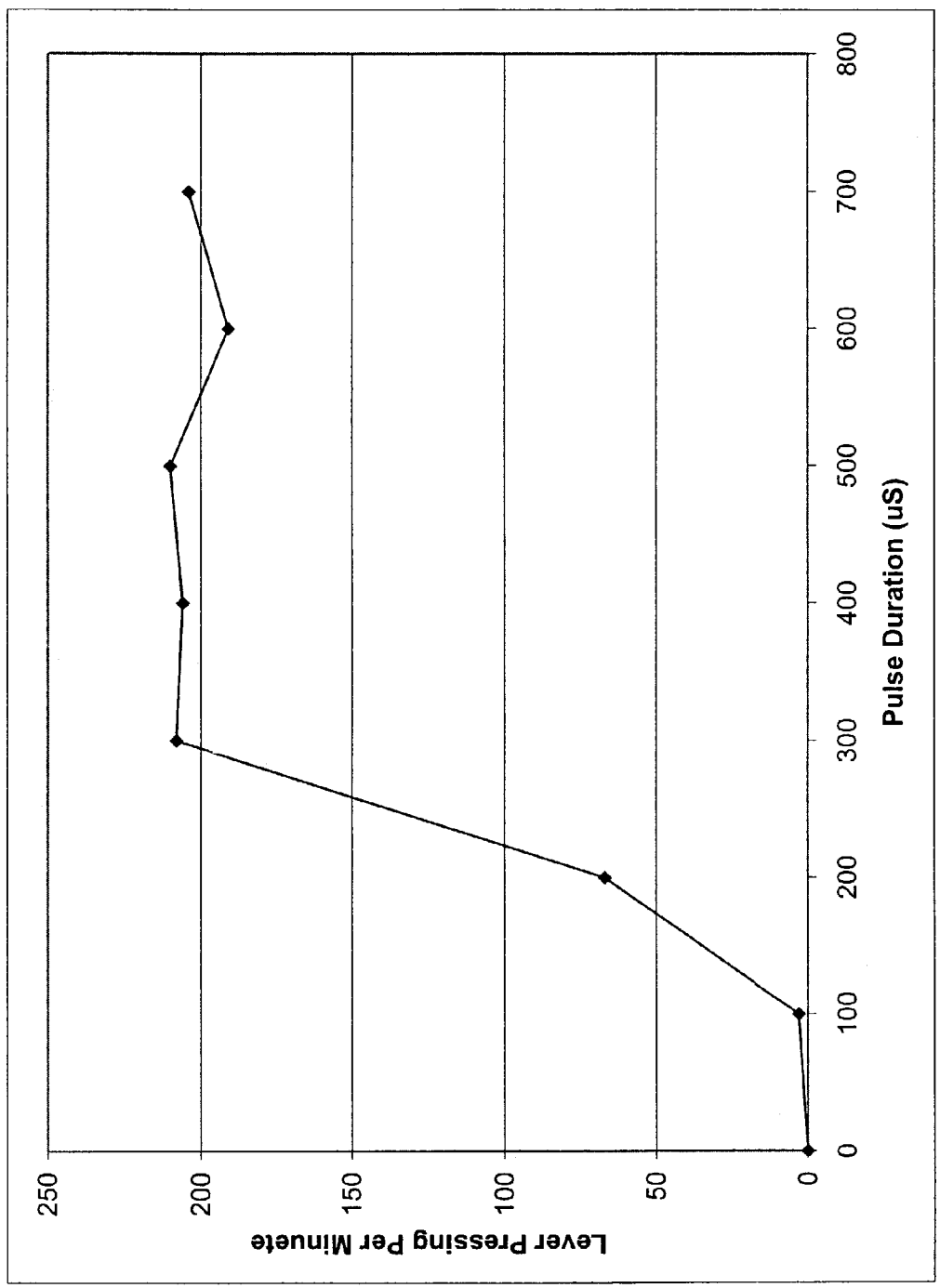
FIG. 6 illustrates a plot showing a number of lever presses per minute by an animal when applying a constant voltage with different pulse durations.

In our experiments, the telestimulation system was used to generate behavioral effects in ways that make it possible to develop new behavioral models for neurophysiology study in freely moving animals. Somatosensory stimulation was used to create percepts that were conditioned to act as cues in a behavioral task reinforced by rewarding medial forebrain bundle stimulation. From the point of view of generating sensory percepts and rewards the fact that system output was a straightforward 5 V TTL pulse train was not a limitation. The effect of a stimulus pulse train at any given brain location depends on pulse amplitude, pulse duration, pulse frequency, and the total number of pulses delivered. Within certain windows these parameters are known to sum linearly. Thus, changing one or more of the three programmable parameters (pulse duration, frequency, and number of pulses) can create variable desired magnitude of stimulation strength. In our study, these stimulus parameters were arranged for optimizing the magnitude of stimulus percepts and rewards (reward magnitude of MFB stimulation was estimated by bar pressing rates in response to parametric variation). As an example, FIG. 6 shows how bar pressing rates, in one of our subjects, changed as a consequence of varying MFB stimulation along a single dimension (data are from a single session).

For the more general brain-stimulation experiment, however, a constant voltage stimulator might be considered inadequate; some experimental situations will require the ability to alter current amplitude at will. If required, this additional capability—to make it function as constant current source—can be also added onto our basic telemetry system with some modification of circuitry. What would be required includes !1) a higher voltage source, (2) constant current circuitry, (3) a variable reference voltage for constant current control of that circuitry (or a hardware set current limit), and (4) an electrode isolation scheme, all small enough to be incorporated into a reasonably sized backpack. As noted above, since this mobile system is floating, it is not necessary to have a split power supply for biphasic stimulation. Requirement (1) could be met with charge pump devices. Requirement (2) could be met with a power transistor in series with a current sensing resistor and controlled by an operation amplifier. Requirement (3) could be met with the Basic Stamp "PWM" instruction, or, if larger microprocessors were to be used, a DAC. Requirement (4) could be met with digital relays, some of which have very high off impedances. One complete solution might be the eight-channel application specific integrated circuit (ASIC) of Troyk, though its current capabilities, as presently configured, may not be adequate for MFB stimulation.

Moreover, the system tested could be modified in the following ways: First, the number of bipolar stimulation channels can be increased to sixteen by using a 32-channel microprocessor. Increasing the baud rate of the serial communication system can markedly reduce the stimulus delay. Alternatively, a look-up table of commonly used stimulation patterns can be stored in the microprocessor's memory, thereby reducing the number of characters that must be sent through the serial port. Major advantages can be obtained by integrating a general-purpose transceiver with a microprocessor capable of handling multi-channel stimulation, and also higher order I/O protocols. This would enable full duplex wireless transmission enabling the delivery of stimulus commands to the animal as well as receiving incoming sensor data if needed. This wireless platform could serve to obtain neurophysiological recordings from the behaving animal. Such a scheme, for example, would be highly useful in studying the neural correlates of navigation while directing freely moving animals.

Specific Applications for Remotely-Guided Animals

The techniques disclosed herein allowing human operators to use wireless remote control to guide instrumented animals such as rats through a range of terrestrial environments open up many practical uses. In fact, such remotely guided animals (RGAs) may be employed for important civilian, military and intelligence applications, such as finding buried humans in collapsed buildings, finding land mines, using stealth to gain intelligence about explosives, drugs, or human targets in buildings, and placing surveillance devices in trees, tunnels, and buildings.

The RGA fills a great need that exists for small robotic devices that can carry a payload into areas that are dangerous, inaccessible, or require stealth. By comparison with currently available small robots, animals exhibit exceptional functionality because evolution has imbued them with great adeptness in handling different earthly terrains. Unlike existing artificial intelligence devices which can be programmed to handle lists of pre-defined tasks, biological intelligence has the innate ability to handle novel real-world conditions. As such, RGAs are capable of great autonomy in their ability to solve specific terrain problems. For example, by simply rewarding animals such as rats for going right, left or straight, by remote control stimulations to the brain, they quickly learned to handle whatever obstacles they encountered. Feral rats are particularly adept at penetrating buildings (e.g., by digging tunnels, squeezing through narrow cracks, chewing through walls or jumping from trees), finding a target (e.g., food), and returning home. One of our overall aims here is to harness such innate capabilities in animals that are also well controlled. Moreover, RGAs carry their own highly developed natural sensors that can be used for homing in on specific targets and for detecting and adapting to novel situations. Rats' olfactory sense is more acute, for example, than any artificial chemosensor. Trained rats could replace dogs, therefore, as sensors for drugs or explosives.

Most importantly, however, animals have excellent "sensor fusion" capabilities, allowing them to combine different senses to detect salient objects in the environment. A particular advantage of rats is that they can use their non-visual senses to traverse complex spaces in the dark. Thus, rats could be trained to find humans trapped in collapsed buildings, for instance. Such humans should be detectable not only by how they look, but also by their scent, sound and feel. RGAs may also be useful for intelligence operations because they are stealthy and naturally occurring. For example, native feral rats could be implanted subcutaneously with appropriate electronic devices, and then trained. Such rats could then be returned to their environment, electronically guided to a particular location, and used to transmit sensor information from that location to a wireless receiving station.

For example, we have configured a system allowing video signals to be returned from a rat to the operator. This system includes a miniature CMOS video camera and a 2.4 GHz telemetry transmitter, both of which are mounted on the animal's backpack. The video camera is mounted on the animal's shoulders to provide a "rat's eye" view of the local environment. The operator uses this feedback to guide his decisions about the direction in which the rat should be directed to turn. A microphone may also be used to obtain audio data. Note that the animal may be guided in real-time by a human operator or automatically under the control of a computer that is programmed to issue appropriate instructions to the animal. The animal may be guided automatically, analogous to an autopilot system for an aircraft. If the animal veers off course or some other anomalous condition is detected, an alarm notification can be made to alert a human operator.

The backpack also includes a 9V Lithium battery pack, a microprocessor with eight digital IO ports, and a 433 Mhz wireless serial modem. Use of a serial modem to control an on-board microprocessor enables a computer program to be downloaded into the microprocessor, where the serial modem is then used to control its application of stimulus trains through its different output ports. When using low impedance electrodes, it is possible to deliver stimuli directly through the microprocessor digital outputs themselves. In general, the stimuli should be from 50-100 microamperes for rats. The stimuli parameters may vary for different animals. The DIO has a 5V, 35 mA output capacity. This is therefore sufficient if the electrodes have about 50 KOhm resistance. Increasing pulse and train width, however, can compensate for the low output voltage.

Possible applications are summarized below.

1—Intelligence: Stealthily penetrate spaces (buildings, encampments, installations). Explore and thereby map the space. Gather specific information about activities in the space using video cameras, microphones, and other sensors. Drop surveillance devices in the space. Use remote communications (RF, ultrasound, existing voice/data networks) to transmit information back to base. Remain for long time periods in the space by foraging for food and water. Harvest electrical power from the environment. Alternatively, quickly return to base, carrying information stored on backpack storage devices.

2—Urban assault: Use rats to penetrate buildings and return intelligence about enemy.

3—Climb trees and other structures carrying equipment for area surveillance~

4—Penetrate tunnel networks: Rats enter tunnels and find areas of human occupation 5—Minefield: Remotely guide rat into suspected minefield. Rat uses olfaction to sense buried mines. When mine chemicals detected, the rat digs to find more chemical; This alerts the operator about the location.

6—Sentries: Rats guided to advance areas carry sensors, and/or are sensors themselves for CBW agents.

7—Drug or munitions sensing—cheaper than dogs. Can use neurophysiological recording in olfactory system to identify odorants.

8—Search and rescue in rubble pile after building collapse. (see below)

9—Enter and return info about hard to enter small spaces in buildings or under streets (HVAC, utility areas, cable conduits, sewers). Find and possibly repair electrical, plumbing, communications problems. Find and possibly remediate colonies of insects, rodents, or other vermin.

10—Climb trees to string Christmas lights.

Further details of possible applications are provided below.

I. Search and Rescue in Collapsed Building.
- A. A building falls because of structural failure, tornado, earthquake, etc.
- B. Rat is pre-trained to home on the scent, sound or sight of human.
- C. Rat is guided to the most likely site of entrance into the rubble pile.
- D. Rat caries electronics apparatus for remote guidance, video with IR illumination, bi-directional audio, and accelerometer and compass for spatial localization.
- E. If human found, video can retrun picture. Through bi-directional audio, have conversation with base.
- F. If rat can drag a tube to the person, can supply water and food through tube
- G. If RF is lost:
  - Use building's residual electronic connections if possible.
  - Rat drags tether with transceiver and water tube as far into hole as possible.
  - Rat swarm is used, with additional rats guided to jettison transceiver repeater units to relay signal to base.
  - Use other transmission medium, e.g., ultrasound.
  - Rat moves autonomously, and returns with info.

II. Search for Buried Landmines
- A. Rats pre-trained to home in on scents of common landmine chemicals.
- B. Upon detecting the chemicals they begin to dig, and continue as scent becomes stronger.
- C. Rats are remotely guided through suspected landmine fields.
- D. Rats carry electronic apparatus for remote guidance, video/audio, GPS, and accelerometer and compass for detection of conditioned digging responses to finding a mine.
- E. Rats are too small to set off mine, but can detect them.
- F. Accuracy of mine detection is enhanced by recording brain activity characteristics of expected reward, or to scent-related neural activity in olfactory lobe.

III. Reconnoiter Buildings in Terrorist or Urban Warfare Situation
- A. Rat is pre-trained to home in on humans while exploring buildings.
- B. Rat with standard instrumentation is remotely guided to a suspect building.
- C. Stealth achieved through darkness and use of appropriate cover.
- D. Rat enters building through holes in walls, windows, doors, basement, roof, or sewer.
- E. Rat explores building to find humans.
- F. If RF is not lost, it returns video/audio and positions of humans.
- G. If RF is lost, it returns to base with pictures and positions of humans.

Experimental Plan

A plan for enhancing RGA technology is provided to enhance the current behavioral, neurophysiological, electronic, communications and computer techniques used to implement RGAs for specific applications. Particular emphasis is placed on the following: 1—N expanding the range of semi-autonomous behaviors that can be elicited though operator guidance, 2—improving the technologies for teleoperation and realtime position sensing, 3—enhancing the sensor capabilities of the RGAs, both though electronic and neurophysiological techniques, 4—developing tools and techniques for coordinating swarms of RGAs, 5—improving the cost and efficiency of RDAs by developing automated training techniques, and 6—improving the RGAs' stealth and longevity by developing subcutaneous implantable electronics for communications, control and energy harvesting. Various factors are provided below.

I Animal
- A. Species
  1. Rat—public relations, stealth, versatility, indoor terrains
  2. Squirrels—arboreal adeptness, stealth
  3. Rabbits—speed, stealth
  4. Coyotes, jackals—public relations, stealth, adeptness
  5. Larger mammals—payload, specific capabilities
  6. Birds—flight, soaring, stealth
- B. Gender
  1. Females—accurate guidance, terrain adeptness
  2. Males—payload, endurance
- C. Size
  1. Max payload about ⅓ of body weight
  2. Genetically large strains
  3. Growth hormone enhanced
- D. 300 g hooded rat female—best for training
- E. 700 g hooded rat male—best for payload
- F. Large strains of rats? Growth hormone?
- G. 700 g feral rat—best for terrain capability and stealth
- H. Other mammal
- I. Bird II. Behavioral
- A. Specific movements
  1. Left/Right
  2. Stop
  3. Rear
  4. Move head to position mini camera
- B. Finding specific targets
  1. Olfactory
  2. Auditory
  3. Type of space, e.g. Open doorway
  4. Living creature, e.g. human
- C. Autonomies
  1. Explore a space, i.e. follow a wall around a building
  2. Go to a buil ding
  3. Go fast straight ahead
  4. Go through a tunnel
  5. Go up a staircase
- D. Terrains
  1. Indoor rooms, hallways
  2. Indoor industrial
  3. Inside walls
  4. Under streets, sewers
- E. Learning, training techniques
  1. Train sequentially, or randomly
  2. Training to handle distractions
  3. Training for autonomous functions
  4. Training for foraging and handling environments
  5. Training for stealth F. Automated training
  1. Accelerometer to sense turning
  2. Reward turning with appropriate timing
III. Neurophysiological
  A. What is best way to do Left/Right command?
    1. SIstim
    2. MIstim
    3. PPstim
    4. Piezoelectric sound
  B. Best way to do higher level commands
    1. Sensory cortical areas
    2. Brain areas matched to command function, i.e. Hypothal for stop●
    3. Use intrinsic brain maps to grade command; whisker—direction
  C. Neurophysiological recording for sensor
    1. Olfactory bulb—smell
    2. Hippocampus—spatial position
    3. Somatosensory vibrissa—aperture shape
  D. Neurophysiological recording for higher functions
    1. VTA, accumbens
    2. Motor command—to control external device
    3. Intention—to communicate with swarm
IV. Neurophysiology Technology
  A. Electrodes
    1. Up to 16 bipolar channels
    2. Spaced multicontact arrays
    3. Platinum or gold contacts
    4. Steroid eluting to prevent bioreaction
  B. Multichannel stimulator
    1. 16 bipolar channels
    2. Handles bipolar or monopolar
    3. Bipolar pulse sequences
    4. Isolated
    5. Programmable current
    6. Programmable pulse trains
    7. Simultaneous stimulations, interlaced
    8. Miniaturized, low power
    9. Subdermally implantable
    10. Hard wired to electrodes for subdermal implantation
  C. Micro controller
    1. Handles full duplex signal transmission from operator or swarm
    2. Controls stimulator
    3. Handles acceleration, position sensing devices
    4. Controls video frame transmission
    5. Controls jettison of sensor devices
    6. Controls data storage in local memory buffer
    7. Handles autonomous functions
    8. Node for swarm coordination
    9. Repeater for swarm signals
  D. Wireless data transceiver
    1. Wireless full duplex serial interface to microcontroller
    2. Intermittent 56K baud
    3. Spread spectrum Beyond the use of RGAs to perform missions, they also provide valuable research models for the development of biomimetic robots. Engineers wishing to understand how animals handle difficult terrain and solve complex problems have already obtained important insights from biomechanical and neurophysiological analyses of animals. RGAs are advantageous in that they can be directed to perform precise experimental procedures. Such tightly controlled experiments will be necessary to truly understand the biological mechanisms underlying animals' extraordinary abilities to handle real world problems.

Moreover, the brains of mammals and birds all possess mesolimbic dopamine fibers in their lateral hypothalamic medial forebrain bundles. This system is considered a final common pathway for reward and motivation. Mild electrical stimulation of this region in birds, as well as mammals can mimic the rewarding effects of physical reinforcers, such as food or water. Thus, different mammalian or avian species could be used for different RGA applications. For example, a remotely guided urban pigeon carrying a small video camera could obtain a wealth of information.

Finally, the use of animals for such purposes is quite humane. Beyond the discomfort associated with recovery from the implant surgery, these animals suffer no pain, and need not be sacrificed. Since the training involves rewards, it is superior to punishment based training methods. Moreover, the use of animals to serve a human need is consistent with the long-established human history of domesticating animal species based on their evolutionary adaptations. Laboratory rodents, which are new symbionts with humans, were domesticated because they are inexpensive, robust and arouse relatively little sentimental attachment in humans. The same qualities make them good candidates for RGA applications.

The invention has been described herein with reference to particular exemplary embodiments. Certain alterations and modifications may be apparent to those skilled in the art, without departing from the scope of the invention. The exemplary embodiments are meant to be illustrative, not limiting of the scope of the invention, which is defined by the appended claims.

What is claimed is:

1. A method for guiding forward, right and left movement of a freely roaming animal, comprising:
   implanting electrodes in a medial forebrain bundle (MFB) area of an animal's brain for controlling the animal's forward movement, and implanting electrodes in a portion of the animal's brain for controlling left and right movements;
   energizing the electrodes to provide cues to the animal to move forward by stimulating the MFB area of the animal's brain to achieve a first actual behavioral result; and
   energizing the electrodes to provide cues to the animal to change its direction of movement either left or right by stimulating the portion of the animal's brain for controlling left and right movement, individually or simultaneously with the step of energizing the electrodes to provide cues to the animal to move forward, to achieve a second actual behavioral result;
   wherein the first actual behavioral result is the animal moving forward for a specified length of time and distance, and the second actual behavioral result is the animal turning left or right for a specified length of time and distance.

2. The method of claim 1, wherein:
   the cues are provided to the animal to coordinate its movements; and
   the portion of the animal's brain for controlling left and right movement includes the somatosensory (SI) cortices of the animal's brain.

3. The method of claim 1, further comprising:
   repeating the energizing of the electrodes in the animal to achieve a first desired behavioral result and a second desired behavioral result.

4. The method of claim 1, further comprising:
   a plurality of respective freely roaming animals wherein each of the plurality of animals has electrodes implanted in the portions of the animal's brain for controlling the animal's forward movement and left and right movements; and energizing the electrodes to provide cues in one or more of the plurality of animals.

5. A system for guiding forward, right and left movement of a freely roaming animal, comprising:

a plurality of electrodes configured to be implanted in a medial forebrain bundle (MFB) area of an animal's brain for controlling the animal's forward movement;

a plurality of electrodes configured to be implanted in a portion of the animal's brain for controlling left and right movements;

an energizing device configured to be coupled to the animal and configured to energize the electrodes to provide cues to the animal to move forward by stimulating the medial forebrain bundle area of the animal's brain, and to provide cues to the animal to change its direction of movement by stimulating the portion of the animal's brain for controlling left and right movements;

a remotely controlled receiver configured to be coupled to the animal and configured to receive signals for controlling the energizing device;

a transmitter configured to initiate the signals for controlling the energizing device;

a first signal initiated from the transmitter configured to energize the plurality of electrodes configured to be implanted in the MFB area for a specified period of time to provide cues to the animal to move forward in a direction; and a second signal initiated from the transmitter individually or simultaneously with the first signal configured to energize the plurality of electrodes configured to be implanted in the portion of the animal's brain for controlling left and right movements for a specified period of time to provide cues to the animal to turn left or right, whereby the animal turns a specified direction and moves forward in a new direction.

6. The system of claim 5, wherein the first signal is initiated and maintained for cueing the animal to move forward for a specified first distance, the first signal is maintained while the second signal is initiated, both the first and second signals being maintained for a specified length of time for turning the animal the specified direction, and the first signal stopped and the second signal continued for cueing the animal forward in the new direction.

7. A method for guiding forward, right and left movement of a freely roaming animal, comprising:

implanting electrodes in a medial forebrain bundle (MFB) area of an animal's brain for controlling the animal's forward movement, and implanting electrodes in a portion of the animal's brain for controlling left and right movements;

energizing the electrodes to provide cues to the animal to move forward by stimulating the MFB area of the animal's brain to achieve a first actual behavioral result;

energizing the electrodes to provide cues to the animal to change its direction of movement either left or right by stimulating the portion of the animal's brain for controlling left and right movement, individually or simultaneously with the step of energizing the electrodes to provide cues to the animal to move forward, to achieve a second actual behavioral result;

energizing the electrodes for cueing the animal to move forward for a specified length of time and distance in a first direction;

energizing the electrodes for cueing the animal to turn left or right for a specified time and distance simultaneously with the step of energizing the electrodes for cueing the animal to move forward; and energizing the electrodes for cueing the animal to move forward in a new direction.

8. The method of claim 7, further comprising:

guiding the animal in a path having multiple changes of direction.

* * * * *